(12) United States Patent
Uhrich et al.

(10) Patent No.: US 8,747,832 B2
(45) Date of Patent: Jun. 10, 2014

(54) BIODEGRADABLE POLYANHYDRIDES WITH NATURAL BIOACTIVE MOLECULES

(75) Inventors: Kathryn E. Uhrich, New Brunswick, NJ (US); Ashley Carbone, New Brunswick, NJ (US); Almudena Prudencio, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 545 days.

(21) Appl. No.: 12/595,591

(22) PCT Filed: Apr. 14, 2008

(86) PCT No.: PCT/US2008/060254
§ 371 (c)(1),
(2), (4) Date: Jun. 16, 2010

(87) PCT Pub. No.: WO2008/128193
PCT Pub. Date: Oct. 23, 2008

(65) Prior Publication Data
US 2010/0272670 A1    Oct. 28, 2010

Related U.S. Application Data

(60) Provisional application No. 60/911,484, filed on Apr. 12, 2007, provisional application No. 60/956,689, filed on Aug. 18, 2007.

(51) Int. Cl.
*A61K 31/765*    (2006.01)
*A61K 47/48*    (2006.01)
*A61K 31/05*    (2006.01)
*A61K 31/165*    (2006.01)

(52) U.S. Cl.
CPC ........... *A61K 47/48192* (2013.01); *A61K 31/05* (2013.01); *A61K 31/165* (2013.01)
USPC ...................................................... 424/78.37

(58) Field of Classification Search
None
See application file for complete search history.

(56) References Cited

U.S. PATENT DOCUMENTS

| | | | | |
|---|---|---|---|---|
| 4,018,826 A | * | 4/1977 | Gless et al. ................. | 525/418 |
| 4,115,169 A | | 9/1978 | Emmons et al. | |
| 5,451,401 A | * | 9/1995 | Zerby et al. ................ | 424/57 |
| 5,747,011 A | * | 5/1998 | Ross et al. .................. | 424/59 |
| 6,316,015 B1 | * | 11/2001 | Rondelez et al. ............. | 424/409 |
| 6,468,519 B1 | | 10/2002 | Uhrich | |
| 6,486,214 B1 | | 11/2002 | Uhrich | |
| 6,602,915 B2 | | 8/2003 | Uhrich | |
| 6,613,807 B2 | | 9/2003 | Uhrich | |
| 6,685,928 B2 | | 2/2004 | Uhrich et al. | |
| 6,689,350 B2 | | 2/2004 | Uhrich | |
| 7,033,578 B2 | * | 4/2006 | Mailland .................. | 424/61 |
| 7,122,615 B1 | | 10/2006 | Uhrich | |
| 7,396,527 B2 | | 7/2008 | Uhrich | |
| 7,411,031 B2 | | 8/2008 | Uhrich et al. | |
| 7,534,852 B2 | | 5/2009 | Uhrich | |
| 7,662,864 B2 | | 2/2010 | Kanamathareddy et al. | |
| 7,666,398 B2 | | 2/2010 | Uhrich | |
| 7,901,705 B2 | | 3/2011 | Roby et al. | |
| 7,985,415 B2 | | 7/2011 | Giroux | |
| 8,017,714 B2 | | 9/2011 | Uhrich | |
| 8,088,405 B2 | | 1/2012 | Uhrich | |
| 8,221,790 B2 | | 7/2012 | Uhrich | |
| 8,232,322 B2 | | 7/2012 | East | |
| 8,241,668 B2 | | 8/2012 | Uhrich | |
| 8,263,060 B2 | | 9/2012 | Uhrich | |
| 2001/0046476 A1 | | 11/2001 | Plochocka | |
| 2003/0096019 A1 | * | 5/2003 | Currie et al. ................. | 424/649 |
| 2004/0038948 A1 | | 2/2004 | Uhrich | |
| 2004/0048754 A1 | * | 3/2004 | Herrmann et al. ............. | 510/101 |
| 2004/0062778 A1 | | 4/2004 | Shefer et al. | |
| 2004/0096476 A1 | | 5/2004 | Uhrich et al. | |
| 2005/0089506 A1 | | 4/2005 | Uhrich | |
| 2005/0113549 A1 | | 5/2005 | Devlin et al. | |
| 2005/0131199 A1 | * | 6/2005 | Uhrich et al. ................ | 528/271 |
| 2005/0226835 A1 | * | 10/2005 | Nakamura et al. ........... | 424/70.1 |
| 2005/0249697 A1 | | 11/2005 | Uhrich et al. | |
| 2005/0260651 A1 | | 11/2005 | Calias et al. | |
| 2006/0013851 A1 | | 1/2006 | Giroux | |
| 2006/0057179 A1 | | 3/2006 | Giroux | |
| 2006/0188546 A1 | | 8/2006 | Giroux | |
| 2007/0098800 A1 | | 5/2007 | Giroux et al. | |
| 2007/0196417 A1 | | 8/2007 | Uhrich | |
| 2010/0291180 A1 | | 11/2010 | Uhrich | |
| 2010/0291181 A1 | | 11/2010 | Uhrich et al. | |
| 2010/0310498 A1 | | 12/2010 | Kanamathareddy et al. | |
| 2011/0022161 A1 | | 1/2011 | Uhrich et al. | |
| 2012/0058155 A1 | | 3/2012 | Uhrich et al. | |

FOREIGN PATENT DOCUMENTS

| | | |
|---|---|---|
| FR | 2839451 | 11/2003 |
| WO | WO 99/12990 | 3/1999 |
| WO | WO 01/28492 | 4/2001 |
| WO | WO 01/41753 | 6/2001 |
| WO | WO 02/09767 | 2/2002 |

(Continued)

OTHER PUBLICATIONS

Brown et al., J. Med. Chem., 1983, 26(9), pp. 1300-1307.*
Prudencio, Almudena; "Biodegradable Polyanhydrides for Controlled Drug Release", Dissertation submitted to the Graduate School—New Brunswick, Rutgers, The State University of New Jersey, 228 pages, Oct. 2006.*
Definition of "Residue", Random House Dictonary via Dictonary. com, 2013.*

(Continued)

*Primary Examiner* — Brian Gulledge
(74) *Attorney, Agent, or Firm* — Viksnins Harris & Padys PLLP

(57) ABSTRACT

The invention provides polymers that include a biologically active molecule and methods for their use.

30 Claims, No Drawings

(56) References Cited

FOREIGN PATENT DOCUMENTS

| WO | WO 02/09768 | 2/2002 |
|---|---|---|
| WO | WO 02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2009/026544 | 2/2009 |

OTHER PUBLICATIONS

Burt, "Essential oils: their antibacterial properties and potential applications in food—a review", *International Journal of Food Microbiology*, 94, 223-253 (2004).

Carbone et al., "Design and Synthesis of Biodegradable Polyanhydrides Based on Plant and Food-Derived Natural Antimicrobials for Biofilm Prevention", *PMSE Preprints 97-F07*, 2 pages (2007).

Carbone et al., "Design and Synthesis of Biodegradable Polyanhydrides Based on Plant and Food-Derived Natural Antimicrobials for Biofilm Prevention", *234th ACS National Meeting*, Boston MA, Aug. 19-23, 2007, poster, 1 page.

Gupta, V.K., Third Party Observations filed in European Application No. 08799782.1, 52 pages, dated May 20, 2011.

Prudencio, A., "Biodegradable Polyanhydrides for Controlled Drug Release", Dissertation submitted to the Graduate School—New Brunswick, Rutgers, The State University of New Jersey, 228 pages (Oct. 2006).

Prudencio, A., et al., "A Novel Approach for Incorporation of Mono-Functional Bioactive Phenols into Polyanhydrides", *Macromolecular Rapid Communications, 30*, 1101-1108, 2009.

Patent Cooperation Treaty, International Search Report and Writtin Opinion for PCT/US08/060254, 13 pages, Jul. 15, 2008.

Souza, E., et al., "Spices: alternative sources of antimicrobial compounds to use in food conservation", *Rev. Bras. Farm.*, 87(1), 22-25, 2006.

Arredondo et al., Effects of Linkers Substitution on Salicylic Acid-derived Poly(anhydride-esters), website of Rutgers, the State University of New Jersey, 16 pages (2001).

Sparks, et al., "Life after Union: Polymers-R-Us", Presentation at Union College, 40 pages (2007).

Uhrich, K.E., "Designing Polymers for Biomedical Applications", Presentation at Division of Engineering & Applied Science, Harvard University, Cambridge, MA, 50 pages (2002).

\* cited by examiner

US 8,747,832 B2

BIODEGRADABLE POLYANHYDRIDES WITH NATURAL BIOACTIVE MOLECULES

PRIORITY OF INVENTION

This application claims priority to U.S. Provisional Patent Application No. 60/956,689, filed 18 Aug. 2007 and to U.S. Provisional Patent Application No. 60/911,484, filed 12 Apr. 2007. The entire content of each of these provisional applications is hereby incorporated herein by reference.

BACKGROUND

Biofilms and bacterial growth are currently a major problem in many industries including food, medicine and personal care. In essentially every field relating to hygiene, prevention of biofilms is a primary concern. Biofilm prevention is particularly important in the food processing industry as the attachment of bacteria and development of biofilms is a major cause of food spoilage and contamination. It is also critical to control biofilms on medical devices, wound care devices, personal care products and within surgical suites. Thus, products useful for inhibiting or preventing biofilm formation and thereby limiting bacterial growth are needed.

Methods to incorporate bioactive molecules with two or more functional groups into polymers have been described in U.S. Pat. No. 7,122,615, U.S. Pat. No. 6,613,807, US 2005/0089506 and US 2003/0035787. However, these methods are directed to bioactive molecules with two functional groups that allow the molecules to be incorporated into the backbone of the polymer.

SUMMARY OF CERTAIN EMBODIMENTS OF THE INVENTION

Applicant has discovered a method to incorporate bioactive molecules into polymers, and in particular polyanhydrides, utilizing only one reactive functional group of the bioactive molecule. This discovery greatly increases the number and diversity of bioactive molecules that can be covalently linked to polyanhydrides.

In one embodiment the invention provides polymer comprising repeating units that form a biodegradable backbone wherein each repeating unit comprises at least two pendant residues of a biologically active molecule.

In one embodiment, the invention provides food products comprising a polymer or composition of the invention.

In one embodiment, the invention provides a confectionery (e.g. a chewing gum) comprising a polymer or composition of the invention.

In one embodiment, the invention provides a method for inhibiting biofilm formation on an area, comprising contacting the area with an effective amount of a polymer or composition of the invention.

In one embodiment, the invention provides a method for inhibiting biofilm formation on an area of the body (e.g., the skin of a mammal such as a human), the surface of a food, a medical device, a table, floor, or an area that comes into contact with a food or a medical device, comprising contacting the area of the body (e.g., the skin of a mammal such as a human), the surface of a food, the medical device, the table, floor, or the area that comes into contact with a food or a medical device with a polymer or a composition of the invention.

In one embodiment, the invention provides a method for inhibiting biofilm on food storage or food processing equipment comprising contacting the food storage or food processing equipment with a polymer or a composition of the invention.

In one embodiment, the invention provides a method for inhibiting biofilm formation on a personal care product, oral care product, feminine hygiene product, or a wound care product, comprising contacting the personal care product, oral care product, feminine hygiene product, or the wound care product with a polymer or a composition of the invention.

In one embodiment, the invention provides polymers and compositions as described herein for use in medical treatment or diagnosis.

In one embodiment, the invention provides the use of a polymer or composition described herein to prepare a medicament useful for treating a microbial infection in a mammal.

In one embodiment, the invention provides the use of a polymer or composition described herein to prepare, coat or impregnate a medical device.

In one embodiment, the invention provides a pharmaceutical composition comprising a polymer of the invention, and a pharmaceutically acceptable carrier.

In one embodiment, the invention provides a composition comprising a polymer as described herein and an acceptable carrier.

The invention also provides processes and intermediates disclosed herein that are useful for preparing polymers and compositions of the invention.

DETAILED DESCRIPTION

The invention provides anhydride polymers having bioactive molecules as a side chain of a polymer. The polymers of the invention have repeating units that comprise residues of two or more bioactive molecules. Accordingly, the polymers of the invention have a high drug loading capacity, which is beneficial.

Bioactive Molecules

Bioactive molecules, also known as bioactives or biologically active molecules, include naturally occurring compounds that are derived from a variety of sources including but not limited to plants, sea creatures, fungi, animals and other microorganisms. Bioactive molecules possess some inherent desirable biological activity, for example, activity directed to macromolecules, cells, tissues, microorganisms, viruses, invertebrates, bacteria, animals, mammals or humans. Sources of bioactive molecules include, for example, essential oils, food, food extracts, plant extracts, natural antimicrobials, nutrachemicals, preservatives, nutraceuticals, phytochemicals and food additives.

In one embodiment of the invention, at least one of the biologically active molecules is an antimicrobial molecule. In one embodiment of the invention, at least one of the biologically active molecules is an antiseptic molecule. In one embodiment of the invention, at least one of the biologically active molecules is an antibiotic molecule.

In one embodiment of the invention, at least one of the biologically active molecules can be obtained from a food. In one embodiment of the invention, at least one of the biologically active molecules can be obtained from a plant. In one embodiment of the invention, at least one of the biologically active molecules can be obtained from an essential oil.

In one embodiment of the invention, at least one of the biologically active molecules is thymol, carvacrol, o-cresol, phenol, guaiacol, eugenol or capsaicin. In one embodiment of the invention, at least one of the biologically active molecules is thymol, carvacrol, eugenol or capsaicin. In one embodiment of the invention, at least one of the biologically active molecules is carvacrol, eugenol, thymol, mescaline, withaferin A, capsaicin, lawsone, lupulone or β-resercyclic acid. In one embodiment of the invention, at least one of the biologically active molecules is carvacrol, eugenol, thymol, mescaline, withaferin A, capsaicin, lawsone, lupulone or β-resercyclic acid, austalol, geraniol, linalool, thujanol, myrcenol, terpineol, menthol, piperitol, borneol or citronellol. In one embodiment of the invention, at least one of the biologically active molecules is thiosalicylic acid, 2-mercaptoethanol, erythro- and threo-3-mercapto-2-methylbutanol, (±)-2-mercapto-2-methylpentan-1-ol, 3-mercapto-2-methylpentan-1-ol, 3-mercapto-2-methylpentanal, 4-mercapto-4-methyl-2-pentanone, (±)ethyl 3-mercaptobutyrate, 2-methylfuran-3-thiol, 2-furylmethanethiol, trans-p-menthane-8-thiol-3-one, furfuryl mercaptan, 1-p-menthene-8-thiol, 8-mercapto-p-menthan-3-one, 3-mercaptopropionic acid or 11-mercaptoundecanoic acid.

In one embodiment of the invention, the polymers incorporate thymol, carvacrol, o-cresol, phenol or guaiacol. In one embodiment of the invention, the, polymers incorporate other food-based bioactives such as eugenol and capsaicin.

In one embodiment the invention provides polyanhydrides with food or nutrachemicals chemically attached as pendant groups.

Polymers of the Invention

The invention provides a polymer comprising repeating units that form a biodegradable backbone wherein one or more repeating unit comprises at least two pendant residues of a biologically active molecule. In one embodiment, the polymer is a polyanhydride. In another embodiment, the polymer is a polyester, polyamide, or a polycarbonate.

In one embodiment of the invention, the polymer can comprise 2, 5, 10, 25, 50, 75, or 100 repeating units. Typically the polymers of the invention have molecular weights of up to about 50,000 amu.

As used herein, a "polyanhydride" is a polymer that has anhydride bonds in the backbone of the polymer. In one embodiment the polyanhydride is formed from monomer units that react to provide the anhydride bonds.

Bioactive molecules are typically incorporated into the polymers of the invention as pendant groups that are not part of the backbone of the polymer. As such, a tracing of the chain of atoms that form the backbone of the polymer would not include the atoms of the residues of the bioactive molecules. In certain embodiments of the invention, the pendant groups can be considered to be sidechains of the polymer. Bioactive molecules can be attached to the remainder of the polymer of the invention through labile (e.g. anhydride, ester, amide or thioester linkages) bonds, that allow for release of the bioloactive molecules upon degradation (e.g. hydrolysis).

In one embodiment, the invention provides a polymer comprising 1 or more units of formula I, II, III, IV, V or VI:

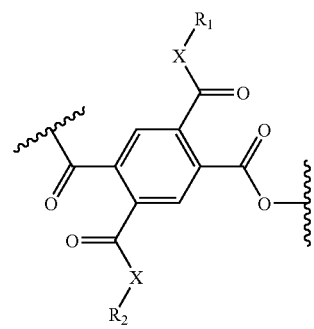

I

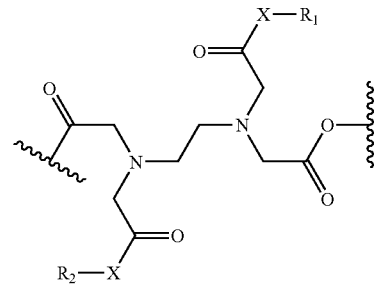

II

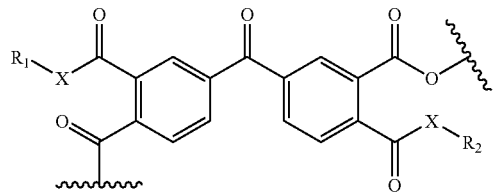

III

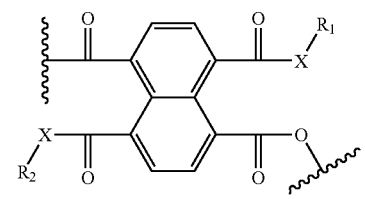

IV

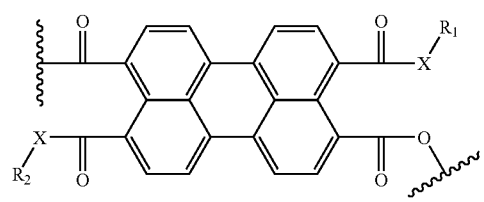

V

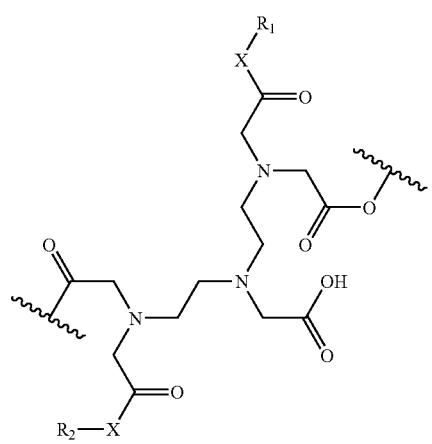

VI wherein;

R$_1$—X— and R$_2$—X— are each independently a residue of a biologically active molecule;

X is O, S or NR$_a$; and

R$_a$ is hydrogen, (C$_1$-C$_6$)alkyl or (C$_3$-C$_6$)cycloalkyl.

In one embodiment of the invention the polymer comprises at least 2 units of formula I, II, III, IV, V or VI. In one embodiment of the invention the polymer comprises at least 5 units of formula I, II, III, IV, V or VI. In one embodiment of the invention the polymer comprises at least 10 units of formula I, II, III, IV, V or VI. In one embodiment of the invention the polymer comprises at least 25 units of formula I, II, III, IV, V or VI. In one embodiment of the invention the polymer comprises at least 50 units of formula I, II, III, IV, V or VI. In one embodiment of the invention the polymer comprises at least 75 units of formula I, II, III, IV, V or VI. In one embodiment of the invention the polymer comprises at least 100 units of formula I, II, III, IV, V or VI. In one embodiment of the invention, the units of formula I, II, III, IV, V or VI are repeating units.

In another embodiment, the invention provides an intermediate of formula Ib, IIb, IIIb, IVb, Vb or VIb:

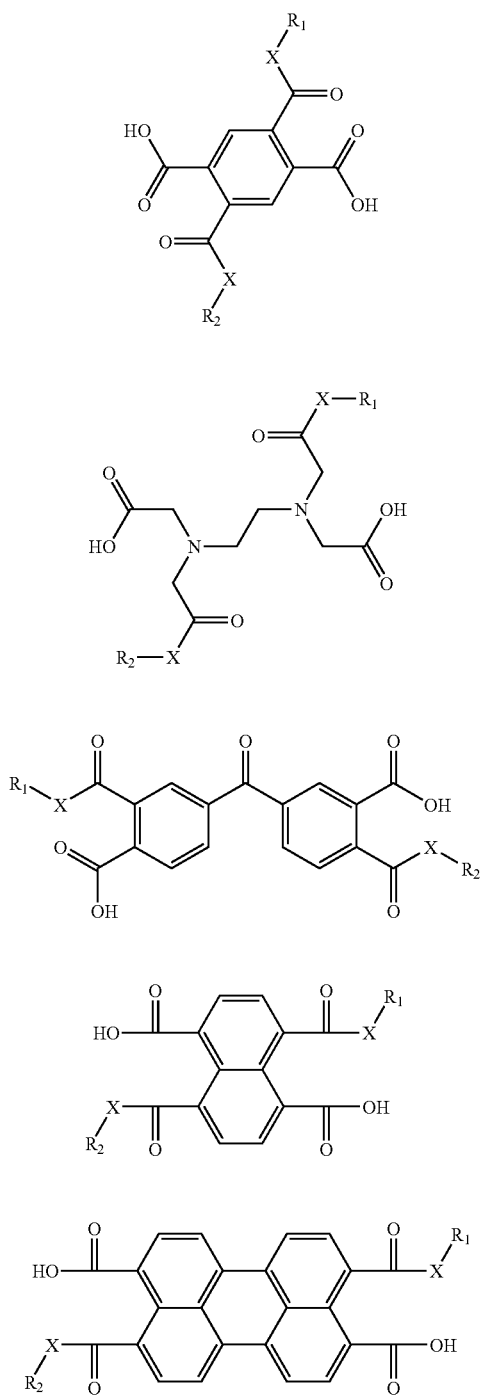

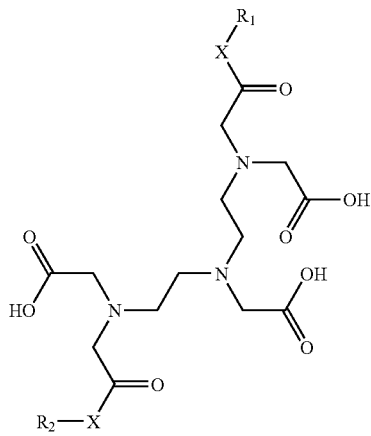

or a salt thereof, wherein:
R$_1$—X— and R$_2$—X— are each independently a residue of a biologically active molecule;
X is O, S or NR$_a$; and
R$_a$ is hydrogen, (C$_1$-C$_6$)alkyl or (C$_3$-C$_6$)cycloalkyl, that is useful for preparing the polymers of the invention.

In one embodiment of the invention the polymer comprises at least two different biologically active residues, i.e. R$_1$—X— and R$_2$—X— differ.

Combinations

Additional bioactive agents can be incorporated into the polymer backbone, included as pendant groups, or dispersed in the matrix of the polymers of the invention. Accordingly, the invention also comprises compositions comprising such combinations.

In one embodiment the invention provides a composition further comprising salicylic acid or salicylsalicylic acid. In one embodiment the invention provides a composition further comprising an antibiotic. In one embodiment the invention provides a composition further comprising at least one of triclosan, propylparaben, nisin, and polylysine. In one embodiment the invention provides a composition further comprising at least one of triclosan, propylparaben, nisin, polylysine ε-polysine, nanomyicin, sorbic acid, wintergreen, polyarginine, chitosan, α-tocoperol, alliin, allicin, ferulic acid, lutein, cichoric acid, cinnamic aldehyde, neral, geranial, citronellal, cuminal, verbenone, thuj one, borneone, pinocamphone, cryptone, carvone, fenchone, piperitone, menthone, estragole, anethole, phtalids, cineole or phellandral.

Preparation of Polymers of the Invention

Polymers of the invention with the bioactives attached as a pendant group can be prepared using standard polymer techniques that are well known in the art for preparing such polymers, e.g. polyesters, polyamides, polycarbonates, and polyanhydrides. For example, representative polymers of the invention can be prepared by melt-condensation polymerization or by solution polymerization techniques starting with appropriate monomers (see *Chem. Rev,* 1999, 99, 3181-3198).

Synthetic procedures for incorporating bioactive molecules with one reactive functional group into polymers have been established and are described herein. In these methods, the bioactive molecule may be attached prior to polymerization, so the number of bioactive molecules attached is well defined. These polymers should typically degrade and release the incorporated bioactive molecules, e.g. to prevent the formation of biofilms. These biodegradable polymers can be formulated into food products and various active food packaging materials. In addition, these polymers may be effective for control of biofilms and bacterial growth in medical devices, oral care and personal care products.

As described herein, di-anhydrides can be ring-opened to generate ester bonds with the bioactive molecules. In some embodiments, symmetrical di-anhydrides are used, which simplifies the chemical characterization, and likely the degradation products of the polymer. Asymmetrical di-anhydrides can also be utilized. In one embodiment of the invention, pyromellitic acid can be incorporated into the polymer of the invention. In one embodiment of the invention ethylenediaminetetraacetic acid can be incorporated into the polymer of the invention. In one embodiment of the invention 3,3',4,4'-benzophenone tetracarboxylic acid can be incorporated into the polymer of the invention. In one embodiment of the invention 1,4,5,8-naphthalene tetracarboxylic acid can be incorporated into the polymer of the invention. In one embodiment of the invention 3,4,9,10-perylenetetracarboxylic acid can be incorporated into the polymer of the invention. In one embodiment of the invention diethylenetriaminepentaacetic dianhydride can be incorporated into the polymer of the invention.

In one embodiment of the invention, aromatic monomers may be used, for easy identification during polymer degradation studies.

The invention also provides methods for preparing polymers of the invention and methods for preparing intermediate diacid monomers that are useful for preparing polymers of the invention. For example, in one embodiment, the invention provides a method for preparing a diacid monomer comprising reacting a bioactive molecule with a symmetrical cyclic pyromellitic dianhydride to provide the diacid with the bioactives attached through ester linkages. In one embodiment, the invention provides a method for preparing a diacid monomer comprising reacting a bioactive molecule with ethylenediaminetetraacetic acid dianhydride to form the diacid, with the bioactives attached through ester linkages. In one embodiment, the invention provides a method for preparing a diacid monomer comprising reacting a bioactive molecule with 3,3',4,4'-benzophenone tetracarboxylic dianhydride to form the diacid, with the bioactives attached through ester linkages. In one embodiment, the invention provides a method for preparing a diacid monomer comprising reacting a bioactive molecule with 1,4,5,8-naphthalene tetracarboxylic dianhydride to form the diacid with the bioactives attached through ester linkages. In one embodiment, the invention provides a method for preparing a diacid monomer comprising reacting a bioactive molecule with 3,4,9,10-perylene tetracarboxylic dianhydride to form the diacid with the bioactives attached through ester linkages. In one embodiment, the invention provides a method for preparing a diacid monomer comprising reacting a bioactive molecule with diethylenetriaminepentaacetic dianhydride to form the diacid, with the bioactives attached through ester linkages.

In one embodiment, the invention provides a method for preparing a diacid monomer comprising reacting a bioactive molecule with a symmetrical cyclic pyromellitic dianhydride to form the diacid, with the bioactives attached through amide linkages. In one embodiment, the invention provides a method for preparing a diacid monomer comprising reacting a bioactive molecule with ethylenediaminetetraacetic acid dianhydride to form the diacid, with the bioactives attached through amide linkages. In one embodiment, the invention provides a method for preparing a diacid monomer comprising reacting a bioactive molecule with 3,3',4,4'-benzophenone tetracarboxylic dianhydride to form the diacid, with the bioactives attached through amide linkages. In one embodiment, the invention provides a method for preparing a diacid monomer comprising reacting a bioactive molecule with 1,4,5,8-naphthalene tetracarboxylic dianhydride to form the diacid, with the bioactives attached through amide linkages. In one embodiment, the invention provides a method for preparing a diacid monomer comprising reacting a bioactive molecule with 3,4,9,10-perylene tetracarboxylic dianhydride to form the diacid, with the bioactives attached through amide linkages. In one embodiment, the invention provides a method for preparing a diacid monomer comprising reacting a bioactive molecule with diethylenetriaminepentaacetic dianhydride to form the diacid, with the bioactives attached through amide linkages.

In one embodiment, the invention provides a method for preparing a diacid monomer comprising reacting a bioactive molecule with symmetrical cyclic pyromellitic dianhydride to form the diacid, with the bioactives attached through thioester linkages. In one embodiment, the invention provides a method for preparing a diacid monomer comprising reacting a bioactive molecule with ethylenediaminetetraacetic acid dianhydride to form the diacid, with the bioactives attached through thioester linkages. In one embodiment, the invention provides a method for preparing a diacid monomer comprising reacting a bioactive molecule with 3,3',4,4'-benzophenone tetracarboxylic dianhydride to form the diacid, with the bioactives attached through thioester linkages. In one embodiment, the invention provides a method for preparing a diacid monomer comprising reacting a bioactive molecule with 1,4,5,8-naphthalene tetracarboxylic dianhydride to form the diacid, with the bioactives attached through thioester linkages. In one embodiment, the invention provides a method for preparing a diacid monomer comprising reacting a bioactive molecule with 3,4,9,10-perylene tetracarboxylic dianhydride to form the diacid, with the bioactives attached through thioester linkages. In one embodiment, the invention provides a method for preparing a diacid monomer comprising reacting a bioactive molecule with diethylenetriaminepentaacetic dianhydride to form the diacid, with the bioactives attached through thioester linkages.

Specific Values

Specific values listed below for radicals, substituents, and ranges, are for illustration only; they do not exclude other values or other values within defined ranges for the radicals and substituents, Specifically, $(C_1-C_6)$alkyl can be methyl, ethyl, propyl, isopropyl, butyl, iso-butyl, sec-butyl, pentyl, 3-pentyl, or hexyl and $(C_3-C_6)$cycloalkyl can be cyclopropyl, cyclobutyl, cyclopentyl, or cyclohexyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, regioisomeric or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

This invention provides polymers that allow an expanded number of bioactive molecules to be chemically incorporated into the polymer structure. Such polymers have applications in a broad range of fields including medical and food-related applications. The polymers can release the bioactive chemically incorporated into the sidechain of the polymer as well as an additional bioactive, e.g., if previously admixed. In some embodiments, the polymers and compositions comprising the polymers are active against *P. aeruginosa, E. coli, Listeria monocytogenes,* or *Salmonella.* In some embodiments, the polymers and compositions comprising the polymers can be applied on medical devices, food, or areas that come into contact with medical devices or food.

Certain embodiments of the invention will now be illustrated by the following non-limiting Example.

Example 1

Preparation of Representative Polymers of the Invention

Polyanhydrides prepared from antimicrobials derived from natural sources such as spices and plant extracts were designed and synthesized (Schemes 1 and 2) (Cowan, M. M. Clinical Microbiology Reviews 1999 12, 564-582) One application of these polymers is their formulation into micro- or nanospheres, which can then be mixed with foods. The polymers could also be used to coat food processing equipment. Alternatively, other bioactive agents can be physically admixed into the antimicrobial-based polyanhydrides to result in a dual action delivery device.

Scheme 1: Natural antimicrobial agents incorporated into polyanhydrides.

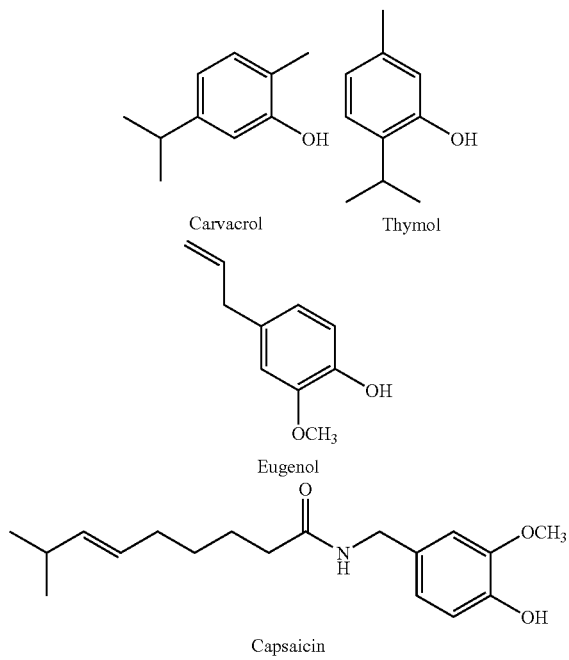

Experimental

Instrumentation.

Polymers and intermediates were characterized by proton nuclear magnetic resonance ($^1$H NMR) and Fourier transform infrared spectroscopy (FTIR). Polymer properties were determined using gel permeation chromatography (GPC) for molecular weights and polydispersity, thermogravimetric analysis (TGA) for decomposition temperatures ($T_d$), and differential scanning calorimetry (DSC) for glass transition ($T_g$) and melting ($T_m$) temperatures.

Synthesis of Polyanhydrides.

Polyanhydrides were synthesized using solution polymerization (Scheme 2) (Domb, A.; Ron, E.; Langer, R. Macromolecules 1988, 21, 1925). In brief, the diacid (6) was prepared by a ring-opening of pyromellitic anhydride (5; 7.5 mmol) with the mono-functional antimicrobial compound (4; 15 mmol) in the presence of a base (e.g., triethylamine; 53 mmol) and in an appropriate solvent (e.g., THF; 40 mL). After the reaction was stirred for 2 h under nitrogen, it was poured over water (~400 mL) and acidified using concentrated HCl. The solid formed (6) was vacuum filtered, washed with water (3×100 mL) and dried under vacuum at room temperature. Diacid (6) (4.6 mmol) was dissolved 20% (w/v) $CH_2Cl_2$ and triethylamine (20 mmol). The reaction was cooled to 0° C. The coupling reagent, triphosgene (5.1 mmol), dissolved in $CH_2Cl_2$ (5 mL) was added drop-wise to the reaction mixture. The reaction was allowed to stir for 2 h at 0° C. under nitrogen. It was then poured over diethyl ether (~100 mL), and the polymer formed (7) was vacuum filtered, washed with acidified water (3×100 mL; pH 2 using concentrated HCl) and dried under vacuum at room temperature.

Scheme 2: Synthetic scheme for the chemical incorporation of a mono-functional antimicrobial (4) into the polyanhydride (7).

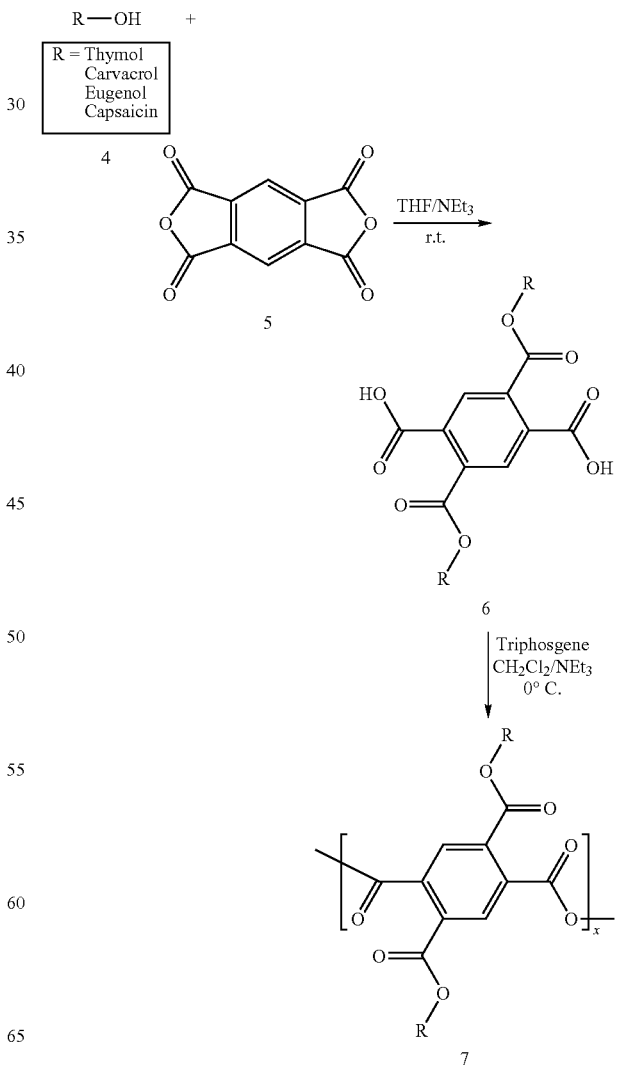

Polymers comprising bioactive molecules linked to the polymer by thioester bonds can be prepared by following the reaction sequence outlined in Scheme 3. For these polymers the ROH (4) starting material is replaced with bioactive molecules of formula RSH. Polymers comprising bioactive molecules linked to the polymer by amide bonds can be prepared by following the reaction sequence outlined in Scheme 3 as well. For these polymers the ROH (4) starting material is replaced with bioactive molecules of formula $RNHR_a$ wherein $R_a$ is hydrogen, $(C_1-C_6)$alkyl or $(C_3-C_6)$cycloalkyl.

Antimicrobial-based polyanhydrides have been successfully synthesized by incorporating the bioactive agent into the polymer backbone via an ester linkage. The polymer drug loadings were 58-60% by weight with nearly uniform polymer chain lengths and a $T_g$ near body temperature (see Table 1).

Due to the instability of the anhydride and ester bonds, these polymers should degrade to release the active antimicrobial compounds.

TABLE 1

| Bioactive | $M_w$ | PDI | $T_d$ (° C.) | $T_g$ (° C.) |
|---|---|---|---|---|
| Thymol | 38,000 | 1.0 | 179 | 37 |
| Carvacrol | 21,700 | 1.0 | 182 | 27 |
| Eugenol | 19,900 | 1.0 | 171 | 58 |

Biofilm Assays on Polymer Surfaces

*S. typhimurium* MAE52 was used to study inhibition of biofilm formation on polymer-coated glass coverslips. The results are depicted in Table 2.

TABLE 2

Pyromellitic Acid Polymers

| Bioactive | Observations |
|---|---|
| Thymol | Prevented cell growth almost completely. |
| Carvacrol | Formed weak biofilms after 24 h. |
| Eugenol | Formed full biofilms after 24 h. |

Polymers based on plant and spice extracts are unique as their components are not synthetic, but natural, antimicrobials. This may be desirable if the polyanhydrides are to be mixed with foods, used in food processing and/or packaging materials.

Conclusions

Biodegradable polyanhydrides with natural antimicrobial properties were synthesized and characterized to be used to inhibit/prevent biofilm formation. Since the polymers can degrade to release the bioactives, they will be very useful in controlled delivery applications for the food industry and other such areas.

Example 2

Preparation of Representative Polymers of the Invention

Polyanhydrides were designed and prepared from antimicrobials derived from natural sources such as spices and plant extracts. Incorporation of these bioactive molecules into the polymers results in biodegradable polyanhydrides that slowly release the bioactive agents to reduce or prevent biofilm formation, e.g., when incorporated into food and food packaging materials.

Plant-Based Polymers

Choice of Bioactive Molecules

Plant and plant extract-based polymers were designed using the natural antimicrobials carvacrol, eugenol, and thymol. Polymers were derived from these bioactive molecules to prevent biofilm formation, e.g., when formulated into food products, food packaging materials and food processing equipment.

Ethylenediaminetetraacetic Acid (EDTA) Polymers

The biocompatible food-grade chelating EDTA was used as a polymer precursor. EDTA is widely used as preservative in packaged foods, vitamins, and personal care products. As depicted below, ring-opening with symmetrical EDTA dianhydride to form diacids with the bioactives attached as ester linkages was performed via procedures similar to those of Example 1.

Scheme 3: Synthetic scheme for the chemical incorporation of an antimicrobial into a representative polymer of the invention.

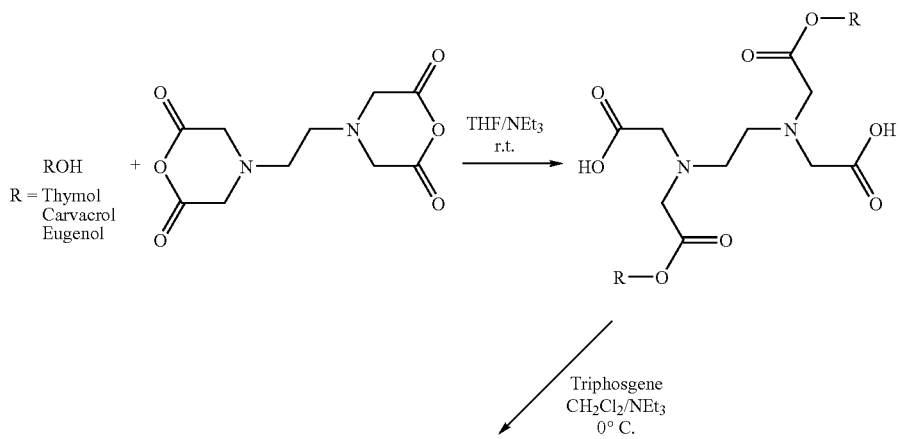

-continued

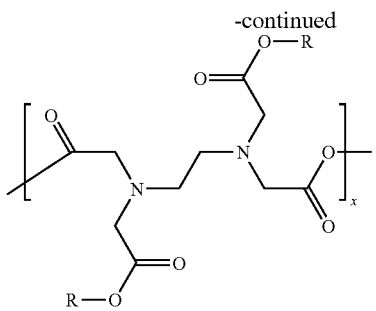

Antimicrobial-based polyanhydrides were successfully synthesized. The polymer drug loadings were 54-56% by weight with nearly uniform polymer chain lengths and a $T_g$ well above body temperature (see Table 3).

TABLE 3

| Bioactive | $M_w$ | PDI | $T_d$ (° C.) | $T_g$ (° C.) |
|---|---|---|---|---|
| Thymol | 23,200 | 1.0 | 223 | 77 |
| Carvacrol | 19,500 | 1.1 | 221 | 65 |
| Eugenol | 11,100 | 1.5 | 229 | 86 |

Biofilm Assays on Polymer Surfaces

*S. typhimurium* MAE52 was used to study inhibition of biofilm formation on polymer-coated glass coverslips. The results are depicted in Table 4.

TABLE 4

| | EDTA Linker |
|---|---|
| Bioactive | Observations |
| Thymol | Formed weak biofilms after 24 h. |
| Carvacrol | Completely prevented biofilm formation. |
| Eugenol | Formed cell aggregates after 32 h. |

The hydrolytic degradation of representative polymers of the invention can be evaluated as described in Example 3.

Example 3

Hydrolytic Degradation of Representative Polymers

Hydrolytic degradation of representative polymers can be studied to determine the rate of release of the natural antimicrobial from the polymer backbone. Polymers will be incubated in PBS (pH 7.4) at 37° C. At predetermined time intervals, the media will be replaced with fresh media, and the spent media will be analyzed by HPLC. See for example: Whitaker-Brothers, K.; Uhrich, K. E. *J. Biomed. Mater. Res.* 2006, 76A, 470-479; Prudencio, A.; Schmeltzer, R. C.; Uhrich, K. E. *Biomacromolecules* 2005, 38, 6895-6901; and Bryers, J. D.; Jarvis, R. A.; Lebo, J.; Prudencio, A.; Kyriakides, T. R.; Uhrich, K. *Biomaterials* 2006, 27, 5039-5048.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A polymer, which is a polyanhydride, comprising repeating units that form a biodegradable backbone wherein one or more repeating unit comprises at least two pendant residues of a biologically active molecule and said backbone comprises 1 or more units of formula I, II, III, IV, V or VI:

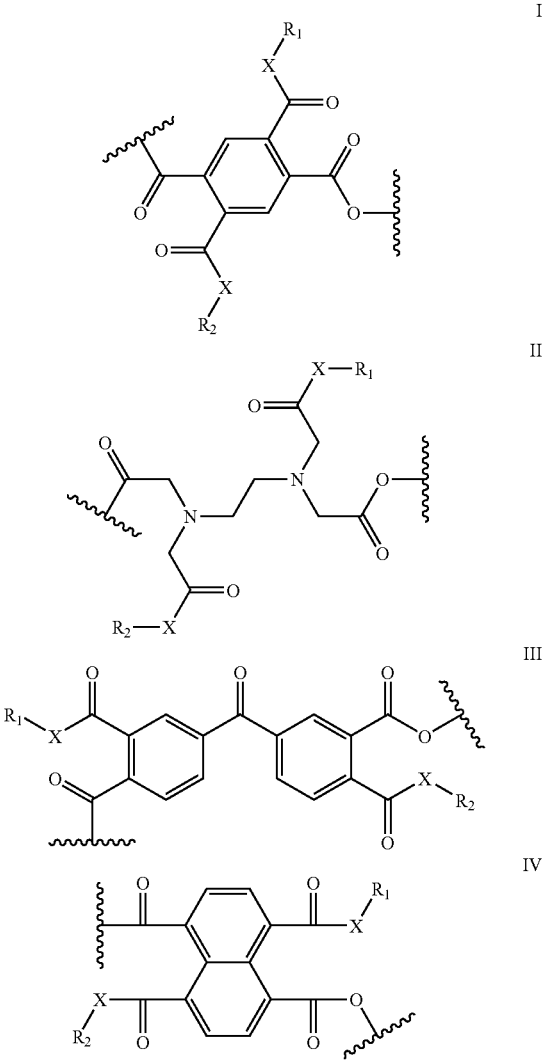

V

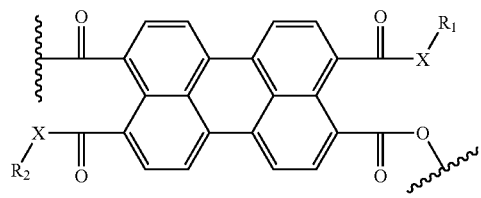

VI

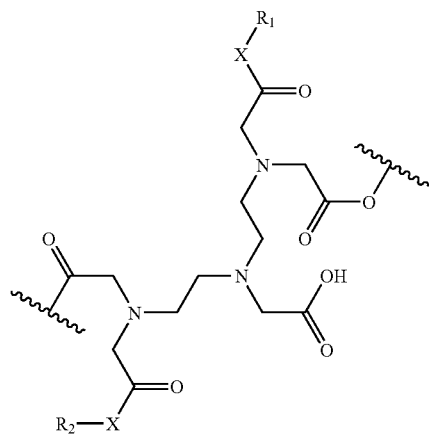

wherein;
R₁—X— and R₂—X— are each independently a residue of a biologically active molecule;
X is O, S or NR$_a$; and
R$_a$ is hydrogen, (C$_1$-C$_6$)alkyl or (C$_3$-C$_6$)cycloalkyl.

2. The polymer of claim 1 wherein each repeating unit comprises at least two pendant residues of a biologically active molecule.

3. The polymer of claim 1 that comprises at least 10 repeating units.

4. The polymer of claim 1 that comprises at least 50 repeating units.

5. The polyanhydride of claim 1 that comprises or more units of formula Ia or IIa:

Ia

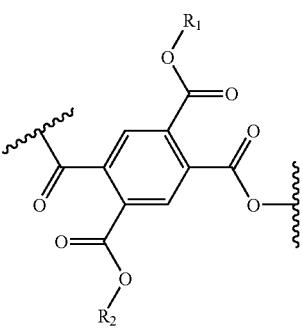

IIa

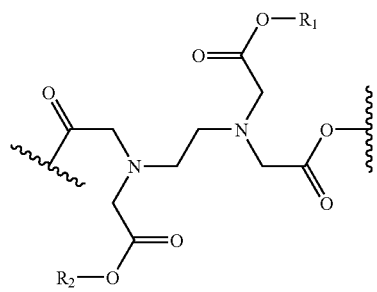

wherein R₁—O— and R₂—O— are each independently a residue of a biologically active molecule.

6. The polyanhydride of claim 1 that comprises or more units of formula Ia, IIa, IIIa, IVa, Va or VIa:

Ia

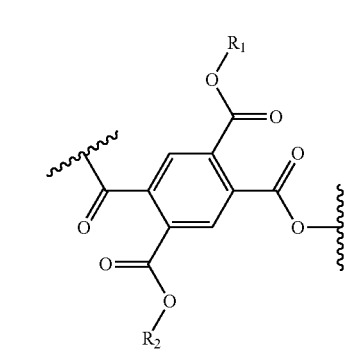

IIa

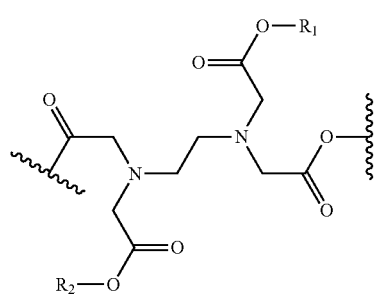

IIIa

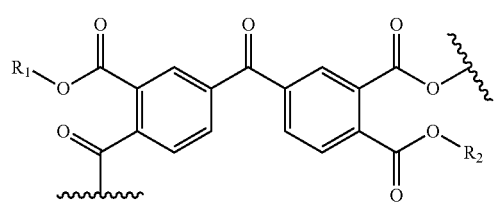

IVa

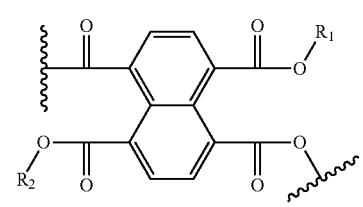

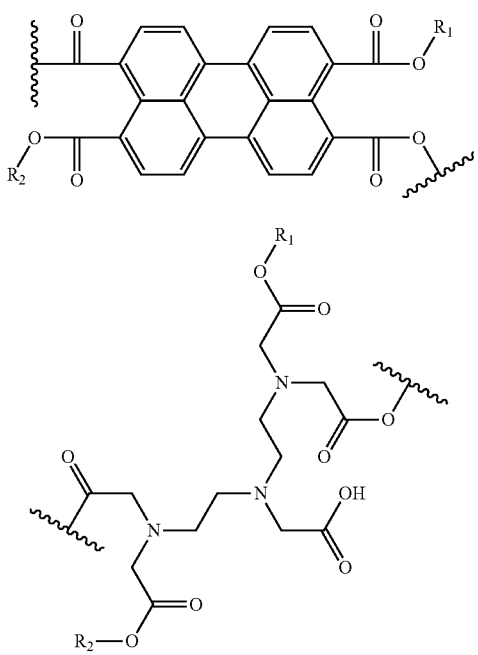

wherein R₁—O— and R₂—O— are each independently a residue of a biologically active molecule.

7. The polymer of claim 1, wherein at least one of the biologically active molecules is an antimicrobial molecule.

8. The polymer of claim 1, wherein at least one of the biologically active molecules is an antiseptic molecule.

9. The polymer of claim 1, wherein at least one of the biologically active molecules is an antibiotic molecule.

10. The polymer of claim 1, wherein at least one of the biologically active molecules can be obtained from a plant.

11. The polymer of claim 1, wherein at least one of the biologically active molecules can be obtained from an essential oil.

12. The polymer of claim 1, wherein at least one of the biologically active molecules is thymol, carvacrol, o-cresol, phenol, guaiacol, eugenol or capsaicin.

13. The polymer of claim 1, wherein at least one of the biologically active molecules is thymol, carvacrol, eugenol or capsaicin.

14. The polymer of claim 1, wherein at least one of the biologically active molecules is carvacrol, eugenol, thymol, mescaline, withaferin A, capsaicin, lawsone, lupulone or β-resercyclic acid, austalol, geraniol, linalool, thujanol, myrcenol, terpineol, menthol, piperitol, borneol or citronellol.

15. The polymer of claim 1, wherein at least one of the biologically active molecules is carvacrol, eugenol, thymol, mescaline, withaferin A, capsaicin, lawsone, lupulone or β-resercyclic acid.

16. The polymer of claim 1 wherein at least one of the biologically active molecules is thiosalicylic acid, 2-mercaptoethanol, erythro- and threo-3-mercapto-2-methylbutanol, (±)-2-mercapto-2-methylpentan-1-ol, 3-mercapto-2-methylpentan-1-ol, 3-mercapto-2-methylpentanal, 4-mercapto-4-methyl-2-pentanone, (±)ethyl 3-mercaptobutyrate, 2-methylfuran-3-thiol, 2-furylmethanethiol, trans-p-menthane-8-thiol-3-one, furfuryl mercaptan, 1-p-menthene-8-thiol, 8-mercapto-p-menthan-3-one, 3-mercaptopropionic acid or 11-mercaptoundecanoic acid.

17. A pharmaceutical composition comprising a polymer as described in claim 1 and a pharmaceutically acceptable carrier.

18. A composition comprising a polymer as described in claim 1 and an acceptable carrier.

19. The composition of claim 17, further comprising salicylic acid.

20. The composition of claim 17, further comprising salicylsalicylic acid.

21. The composition of claim 17, further comprising an antibiotic.

22. The composition of claim 17, further comprising at least one of triclosan, propylparaben, nisin, polylysine ε-polysine, nanomyicin, sorbic acid, wintergreen, polyarginine, chitosan, α-tocoperol, alliin, allicin, ferulic acid, lutein, cichoric acid, cinnamic aldehyde, neral, geranial, citronellal, cuminal, verbenone, thujone, borneone, pinocamphone, cryptone, carvone, fenchone, piperitone, menthone, estragole, anethole, phtalids, cineole and phellandral.

23. The composition of claim 17, further comprising at least one of triclosan, propylparaben, nisin, and polylysine.

24. A food product comprising the polymer of claim 1.

25. A confectionery comprising the polymer of claim 1.

26. A method for inhibiting biofilm formation on an area, comprising contacting the area with an effective amount of the polymer of claim 1.

27. The method of claim 26, wherein the area is an area of a body, the surface of a food, a medical device, table, floor, personal care product, oral care product, feminine hygiene product, wound care product or an area that comes into contact with a food or a medical device.

28. The method of claim 26, wherein the area is an area of a body, the surface of a food, a medical device, table, floor or an area that comes into contact with a food or a medical device.

29. A medical device comprising the polymer of claim 1.

30. A medical device of claim 28 wherein the polymer is coated onto or impregnated within the device.

* * * * *